United States Patent
Bartoli et al.

(10) Patent No.: US 7,348,320 B2
(45) Date of Patent: Mar. 25, 2008

(54) PLATINUM COMPLEXES CONTAINING CHEMICALLY MODIFIED BILE ACIDS, HAVING ANTITUMOR ACTIVITY

(75) Inventors: Enzo Bartoli, Reggio Emilia (IT); Beniamino Palmieri, Modena (IT); Alessandro Medici, Bologna (IT)

(73) Assignee: ICE s.r.l., Reggio Emilia (IT)

( * ) Notice: Subject to any disclaimer, the term of this patent is extended or adjusted under 35 U.S.C. 154(b) by 162 days.

(21) Appl. No.: 10/970,484

(22) Filed: Oct. 21, 2004

(65) Prior Publication Data

US 2005/0113352 A1   May 26, 2005

(51) Int. Cl.
*A61K 31/58* (2006.01)
*C07J 21/00* (2006.01)

(52) U.S. Cl. .......................................... 514/173; 540/13
(58) Field of Classification Search .................. 540/13; 514/173

See application file for complete search history.

*Primary Examiner*—Barbara P. Badio
(74) *Attorney, Agent, or Firm*—Walter H. Schneider

(57) ABSTRACT

The present invention relates to platinum complexes containing bile acid derivatives having antitumor activity

4 Claims, No Drawings

PLATINUM COMPLEXES CONTAINING CHEMICALLY MODIFIED BILE ACIDS, HAVING ANTITUMOR ACTIVITY

FIELD OF THE INVENTION

The present invention relates to platinum (II) complexes having antitumor activity, in particular platinum (II) complexes in which the ligands are represented by ammonia and a ketal at the 3-position with a dihydroxy bicarboxylic acid.

TECHNOLOGICAL BACKGROUND

From the discovery of cisplatin antitumor properties [B. Rosenberg et al., Nature 205, 698, 1965; 222, 385 (1972)], a number of searches have been focused on the development of platinum complexes having lower toxicity and higher selectivity towards the tumour cells. cis-Platinum is in fact, despite its nephrotoxicity and ototoxicity, particularly effective when used in combined chemotherapies in the treatment of the tumors of testes, ovary, head and neck.

Platinum complexes in which two coordination sites are occupied by amino ligands, whereas the two other coordination sites are occupied by functional groups of a steroid derivative, have been described. In EP 265, 350, Kidani et al. disclose complexes in which the steroids, such as cholic and deoxycholic acids, coordinate the metal through the functional groups present on the D ring. On the hand, Spanish Patent ES 2097085 discloses metal complexes in which coordination by the bile acid takes place through the functional groups present on the side chain at the 17-position.

DETAILED DISCLOSURE OF THE INVENTION

The present invention relates to platinum (II) complexes of formula (1):

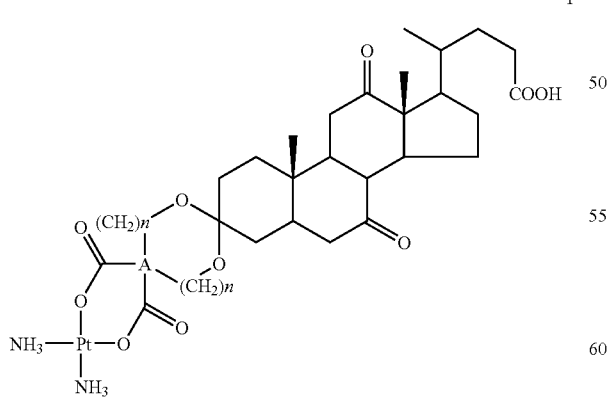

in which n is 0 or 1 and A is C or the CH—CH group.

Preferred embodiments of the invention are the complexes in which:

n is 0 and A is the CH—CH group (compound 1a);

n is 1 and A is C (compound 1b).

Compound (1a) is obtained starting from salt (2), in which M is sodium or potassium,

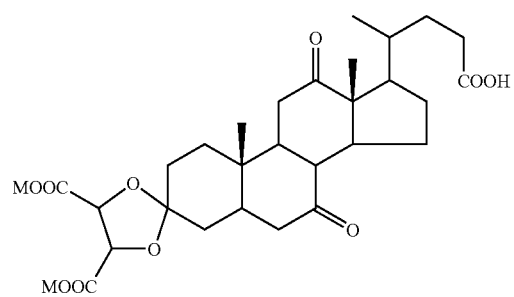

and from the aquocomplex $[(NH_3)_2Pt(H_2O)_2](NO_3)_2$.

The salt (2) is prepared through a synthesis which comprises the following steps:

1) A mixture of dehydrocholic acid (3) and tartaric acid (4) is esterified by heating under reflux in a low molecular weight ROH alcohol selected from methanol, ethanol, propanol, isopropanol, preferably ethanol, in the presence of a sulfonic acid $R^1SO_3H$, preferably methanesulfonic acid (scheme 1), to give a mixture of esters (5) and (6), in which R is methyl, ethyl, propyl or isopropyl, preferably methyl.

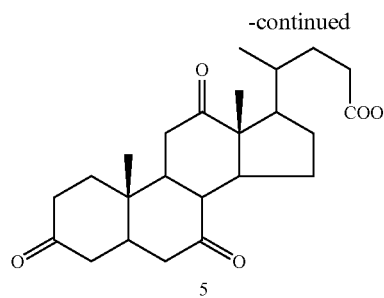
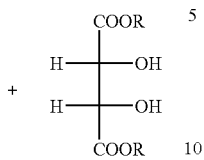
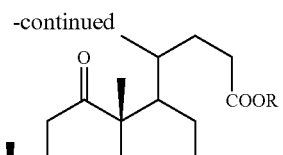

2) The crude from the previous step, consisting of esters (5) and (6), is subjected to heating in benzene or toluene, preferably toluene, to give the ketal of the carbonyl at the 3-position of dehydrocholic acid of formula (7), in which R is as defined above, together with unreacted esters (5) and (6) (scheme 2).

Scheme 2

(5) + (6) $\xrightarrow{\text{Toluene under reflux, 15 hrs}}$

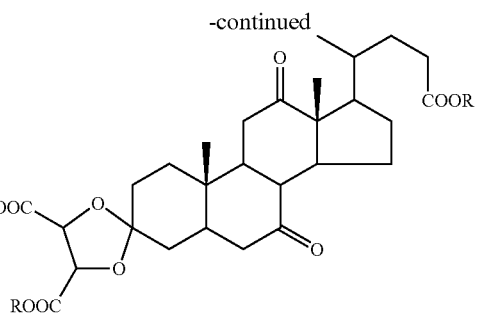

3) The ester mixture from the previous step is saponified by treatment with an alkali hydroxide BOH, wherein B is sodium or potassium, preferably sodium, in a water-alcohol mixture, in which the alcohol is a low molecular weight ROH alcohol selected from methanol, ethanol, propanol, isopropanol, preferably methanol, in which the alcohol-water ratio ranges from 3/1 to 1/1, preferably 2/1, according to Scheme 3.

Scheme 3

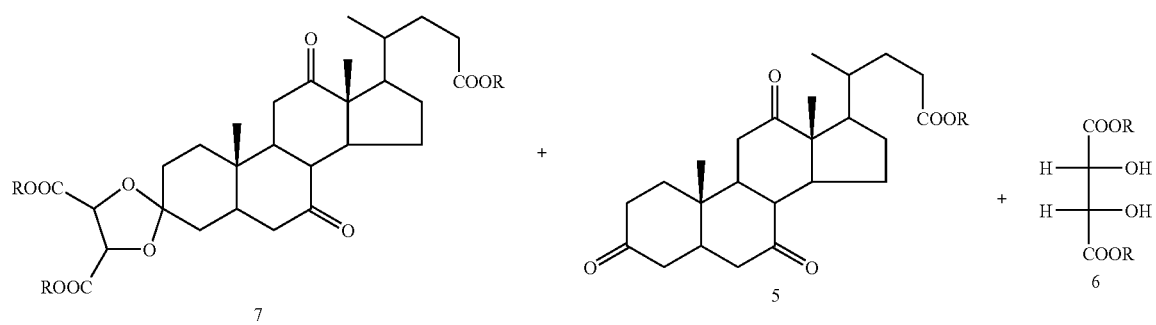

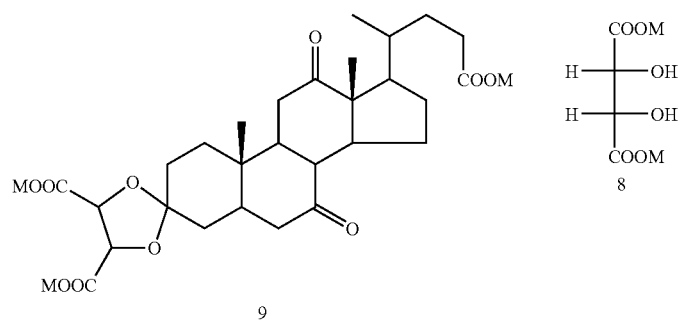

+

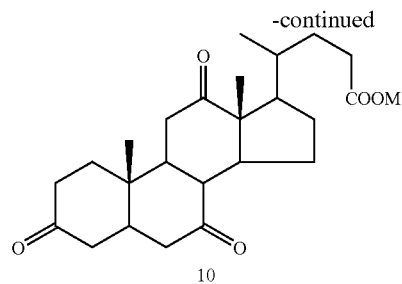

Tartaric acid disodium salt (8) is filtered off the reaction mixture, whereas ketal salt (9) and dehydrocholic acid monosodium salt (10), obtained by evaporation of the water-alcohol phase, are separated by precipitation at different pH, as shown in Scheme 4. Dehydrocholic acid (3) can be obtained by adjusting pH to 5 with an acid selected from, for example, hydrochloric acid, sulfuric acid, methanesulfonic acid and paratoluenesulfonic acid, preferably 20% sulfuric acid, followed by extraction with an organic solvent, preferably ethyl acetate; pH is then further lowered to to approx. 3 to extract the triacid (11a), whereas adjusting pH to values below 2 provides a mixture consisting of diketals (12) and (13).

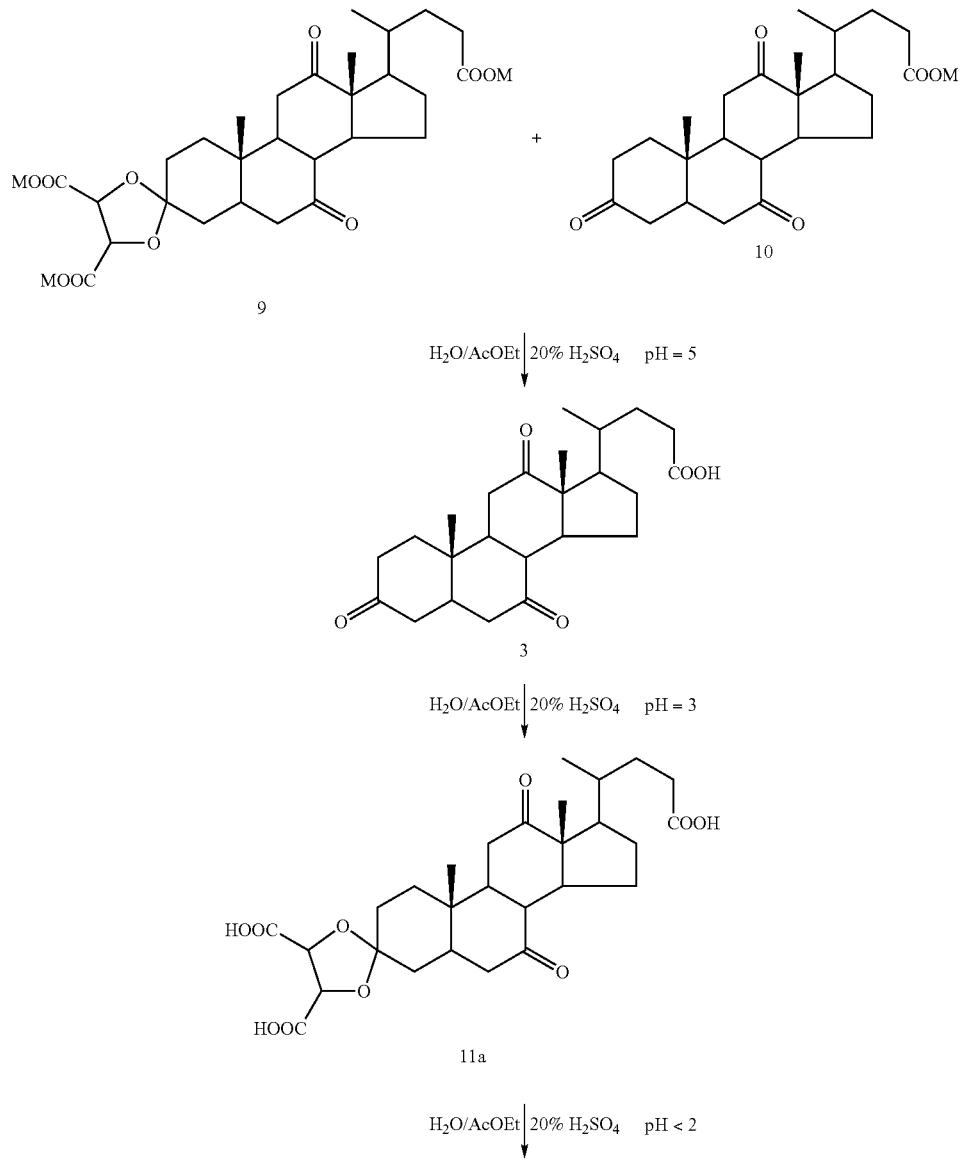

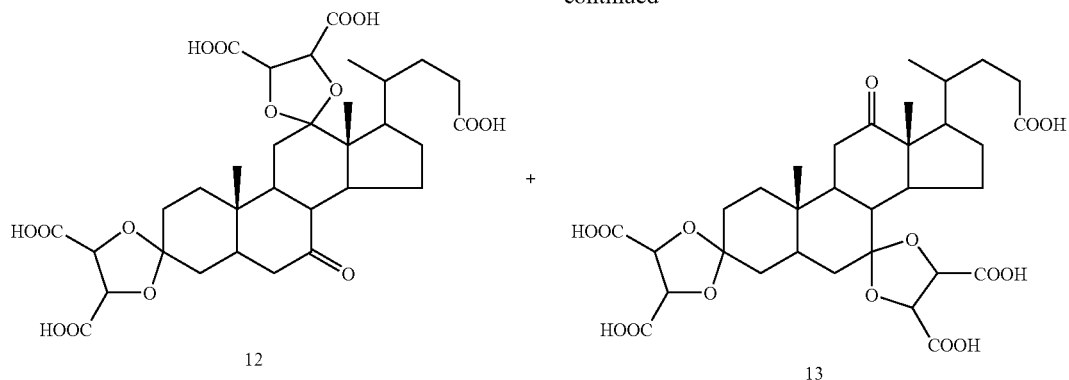

4) By treatment of triacid (11a) with 2 equivalents of MOH hydroxide as defined above, preferably sodium hydroxide, the salt (2) is obtained, which is used for the preparation of the platinum (II) complex (scheme 5).

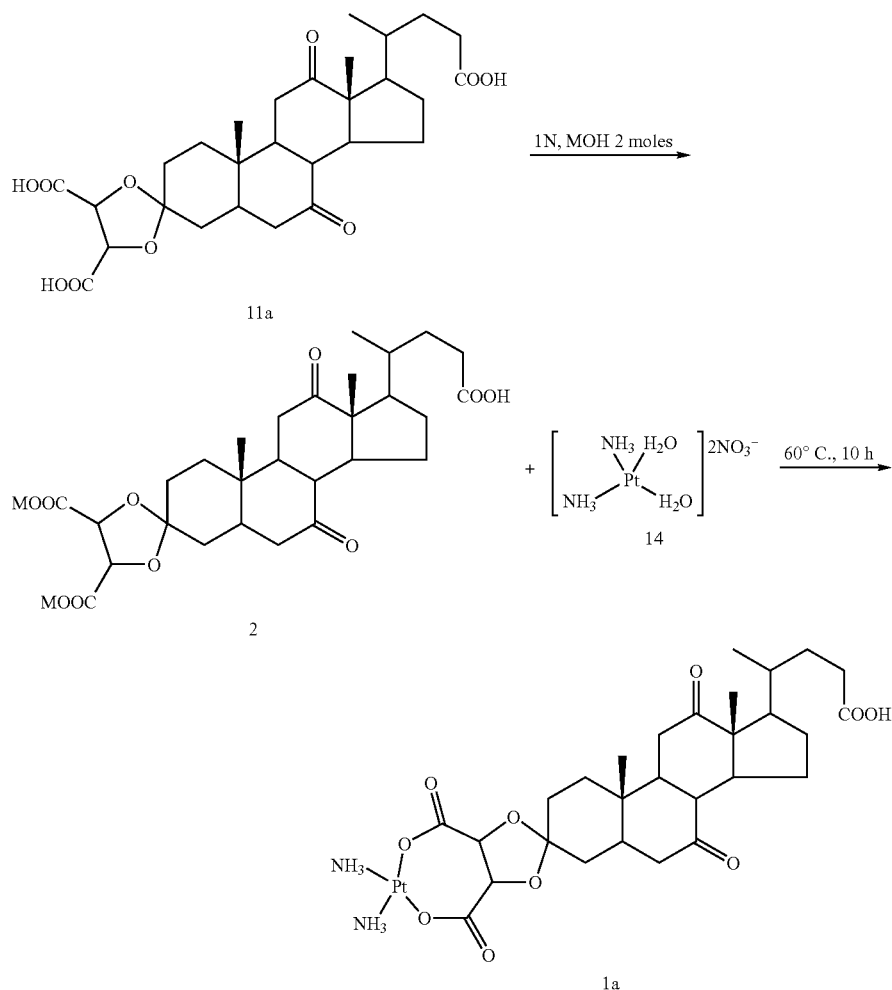

The reaction between aquocomplex (14) and salt (2) is carried out according to the methods conventionally used for the preparation of platinum complexes, while aquocomplex (14) is prepared from cis-platinum according to what described in literature.

Compound (1b) is prepared by reacting salt (15), in which M has the meanings defined above, with aquocomplex (14) (scheme 6):

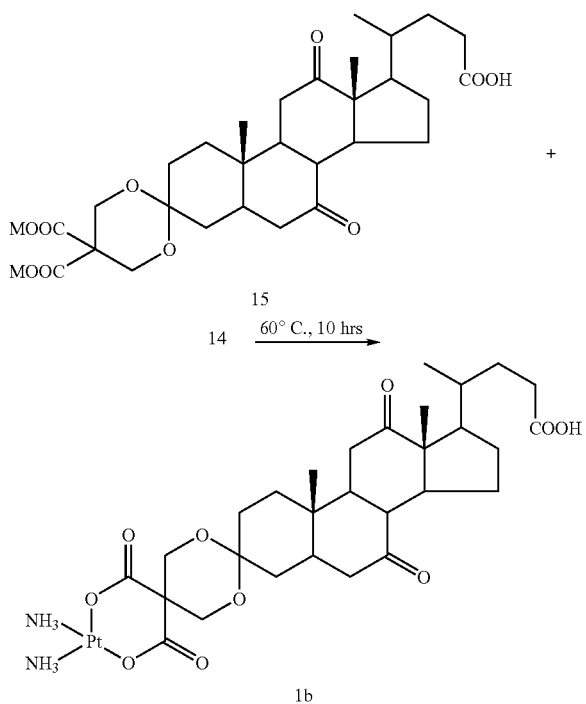

Salt (15) is obtained from triacid (11b), which is prepared according to Scheme 7.

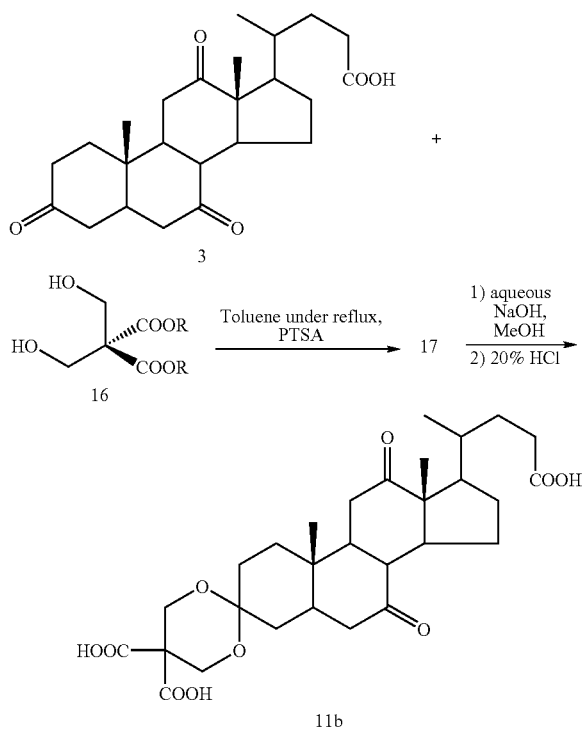

Dehydrocholic acid is reacted with a bis(hydroxymethyl) malonic acid ester (16), in which R has the meanings defined above, in toluene under reflux in the presence of a sulfonic acid, preferably para-toluenesulfonic acid, to give the corresponding ketal of formula (17). Hydrolysis with sodium hydroxide in methanol and subsequent treatment with 20% hydrochloric acid yield the triacid of formula (11b).

Compounds (1), when administered to humans or animals bearing tumors which can be treated with cisplatin or are resistant to cisplatin, are capable of inducing the regression of said tumors.

Compounds (1) can be used for the treatment of those pathological conditions for which cisplatin is used, in particular for the treatment of tumors [Douple et al. Cisplatin Current Status and Developments, Ed. A. W. Prestayk et al., Academic Press, 125 (1980; Douple et al. Platinum Metals Res., 29; 118 (1985)].

Therefore, the present invention also relates to pharmaceutical compositions containing a therapeutically effective amount of a compound of formula (1) in mixture with conventional carriers and excipients.

The effective dose of compounds (1) will be determined by the expert physician according to conventional methods. The relationship between the dosages used for animals of various species and size and those for the humans (based on mg/m$^2$ body area) is described by Freirech et al., Quantitative Comparison of Toxicity of Anticancer Agents in Mouse, Rat, Hamster, Dog, Monkey and Man Cancer Chemother. Rep, 50, n. 4, 219-244 (1986). The patient will receive doses of the complex ranging from 0.1 to 200 mg/kg body weight, with a dosage regimen which will vary depending on a number of factors, well known to the skilled clinician, and the treatment regimen will vary depending on the type of tumor to treat and the conditions of the patient.

Compounds (1) can be administered through the oral, parenteral, topical or intratumoral routes.

The pharmaceutical compositions for the parenteral administration comprise saline sterile solutions or suspensions or sterile powders for the extemporaneous preparation of solutions or suspensions. The pharmaceutical compositions for the parenteral administration also comprise oily preparations for the intramuscular or intraperitoneal administration.

The pharmaceutical compositions for the oral administration comprise, for example, syrups or similar liquid forms, as well as solid forms such as tablets, capsules and the like.

The pharmaceutical compositions according to the present invention are prepared following conventional methods, such as those reported in Remington's Pharmaceutical Sciences Handbook, XVII Ed., Mack Pub., N.Y., U.S.A.

Compounds (1) may be administered together with one or more agents which enhance their antitumor activity or which alleviate the side effects accompanying platinum complexes therapy, for example together with reduced glutathione, as disclosed in GB 2.174.905 and in U.S. Pat. No. 4,871,528.

Complexes (1) can also be advantageously administered together with other platinum complexes having antitumor activity, therefore a farther object of the present invention are pharmaceutical compositions containing compounds (1) in combination with a platinum complex with antitumor activity.

The present invention further relates to the use of compounds (1) for the preparation of pharmaceutical compositions for the treatment of mammals affected with tumors which can be treated with cis-platinum or are resistant to cis-platinum.

The invention is illustrated in greater detail by the following examples.

EXAMPLES

Materials and Methods $^1$H-NMR spectra were recorded with a Varian Gemini spectrometer 300 MHz at the frequency of 300 MHz. Chemical shifts are expressed in ppm.

$^{13}$C-NMR spectrum of triacid (11a) was recorded with a Varian Gemini spectrometer 300 MHz at the frequency of 75.1 MHz. Chemical shifts are expressed in ppm.

Infrared spectra were recorded in KBr with a NICOLET 510P Fourier transformed spectrophotometer.

Example 1

Synthesis of Cholic Acid and L(+)Tartaric Acid 3-Ketal

Preparation 1a—Synthesis of Dehydrocholic and L(+)Tartaric Acid Ethyl Ester 25 g (1 mol) of dehydrocholic acid are dissolved in 200 ml of ethanol, in a 250 ml round-bottom flask equipped with magnetic stirrer and cooler, and 28 g (3 mols) of L(+)tartaric acid and 0.4 ml (0.1 mols) of methanesulfonic acid are added thereto.

The mixture is refluxed for about 5-6 hours, following the reaction by TLC (eluent phase: ethyl acetate/cyclohexane/acetic acid: 50/50/1): disappearance of dehydrocholic acid and formation of two novel products, having Rf value higher than dehydrocholic acid, are observed.

After completion of the reaction, the mixture is cooled and ethanol is evaporated off under reduced pressure, to obtain a white solid.

Preparation 1b—Ketal Synthesis

The white solid from the previous step is taken up into 150 ml of toluene, added with 0.4 ml (0.1 mols) of methanesulfonic acid, then refluxed in a Dean Stark apparatus for 10 hours.

The reaction is followed by TLC (eluent phase: ethyl acetate/cyclohexane/acetic acid: 50/50/1), disappearance of dehydrocholic acid ethyl ester is observed.

After completion of the reaction, the mixture is cooled and toluene is evaporated off under reduced pressure, to obtain a dark brown oil.

Preparation 1c—Saponification Reaction and Acidification

The oily residue from the previous step is treated with 25 g (0.63 mols) of NaOH dissolved in 100 ml of CH$_3$OH and 100 ml of water. Saponification takes place immediately with formation of a white precipitate consisting of sodium tartrate, which is filtered through a porous septum and washed with 60 ml of CH$_3$OH. The filtrate is concentrated in rotary evaporator and the resulting dark solid is taken up into 200 ml of water and 100 ml of ethyl acetate. The diphasic system is treated with 20% H$_2$SO$_4$; the organic phase is separated at pH 5, dried and concentrated, thereby recovering the unreacted dehydrocholic acid.

The aqueous phase is added with a further 100 ml of ethyl acetate and adjusted to pH 2.5-3 with 20% H$_2$SO$_4$; the triacid precipitates and is immediately extracted in the organic phase. The latter is separated and dried; in a short time, crystallization of the triacid (usually as pale brown crystals) is observed.

The aqueous phase is treated with 20% with H$_2$SO$_4$ to pH 1 to obtain a precipitate mainly consisting of dehydrocholic acid 3,7-diketal and 3,12-diketal.

Preparation 1d—Crystallization of Triacid in Ethyl Acetate 20 g of the crude acid from the first crystallization are dissolved in 200 ml of ethyl acetate and 15 ml of water, in a 250 ml round-bottom flask. The resulting brown solution contains a residue of the same color, which is filtered off. The solution is dried over sodium sulfate and evaporated under reduced pressure, remarkably reducing its volume, then cooled and left to stand for some hours, thus precipitating the triacid as a white solid, which is filtered and washed with ethyl acetate. After drying, 13.4 g of triacid is obtained (crystallization yield: 67%).

$^1$H-NMR (pyridine-d$_5$+D$_2$O): 1.06-1.13 (6H, d-s, 21/18-CH$_3$); 1.36 (3H, s, 19-CH$_3$); 1.4-2.6 (m, aliphatic CH and CH$_2$); 2.8 (1H t, 11-CH); 2.98-3.1 (2H, m, 6/8CH); 5.4 (2H m (d,d), 25/26 CH).

$^1$H-NMR (CD$_3$COOD+D$_2$O): 0.9 (3H, d, 21-CH$_3$); 1.19 (3H, s, 18-CH$_3$); 1.45 (3H, s, 19-CH$_3$); 1.5-2.6 (m, aliphatic CH, CH$_2$); 2.9 (1H, t, 11-CH); 3.1 (2H, m, 6/8-CH); 4.95 (2H, m (d,d), 25/26-CH).

$^{13}$C-NMR (pyridine-d$_5$+D$_2$O): 141.4 (C-1); 140.9 (C-8); 132.0 (C-4); 128.5-126.6 (C-aromatics); 81.9 (C-7); 62.9 (C-14); 55.14 (C-15) 52.43 (C-16); 22.16 (C-17); 21.23 (C-18).

IR (cm$^{-1}$): 2980-2900 (aliphatic system v-CH;CH$_2$;CH$_3$ stretching); 1750-1770 (uncoordinated vC=O stretching); 1715-1700 (dehydro carbonyls vC=O stretching); 1400 (d-CH;CH$_2$;CH$_3$ aliphatic system bending); 1250-1300 (vC—O stretching of uncoordinated carboxyls).

Elemental analysis (calculated for C$_{28}$H$_{38}$O$_{10}$)

Calculated value: C, 62.90%; H, 7.16%; O, 29.94%.

Found value: C, 62.81%; H, 7.64%; O, 29.55%.

Preparation 1e—Synthesis of Aquocomplex [(NH$_3$)$_2$Pt(H$_2$O)$_2$](NO$_3$)$_2$ 0.75 g (1.0 mols) of (NH$_3$)$_2$PtCl$_2$ are suspended in a flask shielded from light, containing 20 ml of water; the suspension is added drop by drop, under stirring, with a solution of 0.84 g (2.0 mols) of AgNO$_3$ in 5 ml of water. After completion of the addition, the flask is placed in a bath thermostatized at 60° C. and stirring is continued for 4 hours, after that the mixture is left to cool and silver chloride is filtered off.

A clear, pale yellow filtrate is obtained containing the aquocomplex [(NH$_3$)$_2$Pt(H$_2$O)$_2$](NO$_3$)$_2$.

Preparation 1f—Triacid Disodium Salt 2.0 mols of 1 N NaOH are added, under stirring, with 1.33 g (1.0 mols) of triacid, adding some ml of water to assist stirring.

The solution containing the salt is used as such in the subsequent step.

Preparation 1g—Formation of cis-[diamino-(3-dehydro-cholanoylidene-L-tartrate)platinum (II)]

The hot solution of the triacid disodium salt is added with the aquocomplex solution; a white-yellow flaky precipitate forms. The reaction mixture is kept under stirring in a bath thermostatized at 60° C. for 10 hours.

The precipitate is filtered with suction and left to dry in the air, or in a static dryer at a temperature of 100° C.

1.56 g of complex are obtained (yield: 84%).

$^1$H-NMR (CD$_3$COOD+D$_2$O 2:1) 0.9 (3H, d, 21-CH$_3$); 1.19 (3H, s, 18-CH$_3$); 1.45 (3H, s, 19-CH$_3$); 1.5-2.6 (m, aliphatic CH, CH$_2$); 2.9 (H, t, 11-CH); 3.1 (2H, m, 6/8-CH) 4.2 (6H, s, NH$_3$); 4.8 (2H, m (d,d), 25/26-CH).

IR (cm$^{-1}$): 3285-3270 (vN—H stretching); 2980-2900 (stretching of the aliphatic system v-CH; —CH$_2$; —CH$_3$); 1715-1700 (vC=O stretching of dehydro carbonyls); 1650-1600 (vC=O stretching of coordinated carboxyls); 1350-1380 (vC=O stretching of coordinated carboxyls).

Elemental analysis (calculated for C$_{28}$H$_{42}$O$_{10}$PtN$_2$)
Calculated value: C, 44.15%; H, 5.52%; N, 3.68%.
Found value: C, 41.26%; H, 6.24%; N, 4.00%.

Example 2

Cholic Acid and Bis(hydroxymethyl)-Malonic Acid 3-Ketal Trimethyl Ester $^1$H-NMR (CD$_3$OD): 0.8 (3H, d, 21-CH$_3$); 1.1 (3H, s, 18-CH$_3$); 1.25 (3H, s, 19-CH$_3$); 1.5-2.5 (m, aliphatic CH, CH$_2$); 2.65 (H, t, 11-CH); 2.8 (2H, m, 6/8-CH); 3.6-3.8 (9H, 3s, 29/30/31-CH$_3$); 4.3 (4H, m (d,d), 25/26-CH$_2$).

The invention claimed is:

1. Platinum (II) complex of the formula:

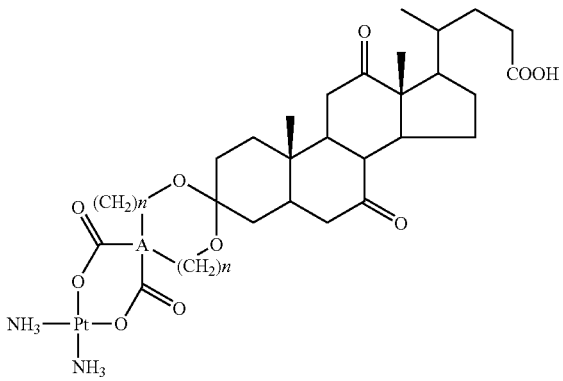

in which n is 0 or 1 and A is C or the CH—CH group.

2. Complex as claimed in claim 1 wherein n is 0 and A is CH—CH.

3. Complex as claimed in claim 1 wherein n is 1 and A is C.

4. Pharmaceutical compositions containing the complex as claimed in claim 1 in mixture with suitable carriers and excipients.

* * * * *